United States Patent [19]

Donlon

[11] Patent Number: 5,755,687
[45] Date of Patent: May 26, 1998

[54] METHODS AND DEVICES FOR OCCLUDING A PATIENT'S ASCENDING AORTA

[75] Inventor: Brian S. Donlon, Los Altos Hills, Calif.

[73] Assignee: Heartport, Inc., Redwood City, Calif.

[21] Appl. No.: 831,102

[22] Filed: Apr. 1, 1997

[51] Int. Cl.⁶ .............................................. A61M 31/00
[52] U.S. Cl. ........................... 604/53; 604/102; 600/18
[58] Field of Search ...................... 600/18; 604/96–102, 604/49, 52, 53, 51; 606/192, 194

[56] References Cited

U.S. PATENT DOCUMENTS

| Re. 33,258 | 7/1990 | Onik et al. |
| 150,960 | 5/1874 | Isbell |
| 231,601 | 8/1880 | Meigs |

(List continued on next page.)

FOREIGN PATENT DOCUMENTS

| 0 103 546 | 3/1984 | European Pat. Off. |
| 0 335 205 | 1/1985 | European Pat. Off. |
| 0 161 045 | 11/1985 | European Pat. Off. |
| 0 218 275 | 4/1987 | European Pat. Off. |
| 0 249 338 | 5/1987 | European Pat. Off. |
| 0 238 106 | 9/1987 | European Pat. Off. |
| 0 277 367 | 8/1988 | European Pat. Off. |
| 0 321 614 | 6/1989 | European Pat. Off. |
| 0 350 302 | 7/1989 | European Pat. Off. |
| 0 357 003 | 3/1990 | European Pat. Off. |
| 0 414 350 | 6/1990 | European Pat. Off. |
| 2246526 | 3/1973 | Germany |
| 334404 | of 1936 | Italy |
| 1271508 | 11/1986 | U.S.S.R. |
| 1371701 | 2/1988 | U.S.S.R. |
| 1097881 | 3/1965 | United Kingdom |
| 1097882 | 3/1965 | United Kingdom |
| 1284701 | 4/1971 | United Kingdom |
| 1414344 | 5/1973 | United Kingdom |
| 1467976 | 3/1974 | United Kingdom |
| 1477665 | 4/1974 | United Kingdom |
| 2056023 | 3/1981 | United Kingdom |
| WO 81/03613 | 12/1981 | WIPO |
| WO 83/03204 | 9/1983 | WIPO |
| WO 89/10155 | 11/1989 | WIPO |
| WO 91/10456 | 7/1991 | WIPO |
| WO 91/17720 | 11/1991 | WIPO |
| WO 92/17118 | 10/1992 | WIPO |
| WO 93/07927 | 10/1992 | WIPO |
| WO 95/30447 | 11/1995 | WIPO |

OTHER PUBLICATIONS

Andersen et al., "Transluminal Implantation of Artificial Heart Valves ... " *European Heart Journal*, 1992;13:704–708.

Baxter Healthcare Corporation. "Fogarty Occlusion Catheter: Instructions for Use," ©1994.

Buckberg, G.D., "Strategies and Logic of Cardioplegic Delivery to Prevent, Avoid, and Reverse Ischemic and Reperfusion Damage," *J Thorac Vasc Surg*, 1987; 93:127–129.

Corday et al., "Symposium on the Present Status of Reperfusion of the Acutely Ischemic Myocardium. Part I," *J. Am Coll Cardiol*, 1983; 1(4):1031–1036.

Cosgrove, "Management of the Calcified Aorta: An Alternative Method of Occlusion," *Ann Thorac Surg*, 1983;36:718–719.

Crooke et al., "Biventricular Distribution of Cold Blood Cardioplegic Solution Administered by Different Retrograde Techniques," *J Cardiac Thorac Surg*, 1991;102(4):631–636.

Datascope FDA 510(k) Application, "Percluder–DL Occluding Balloon," Oct. 12, 1993.

(List continued on next page.)

*Primary Examiner*—Michael Powell Buiz
*Assistant Examiner*—Deborah Blyveis
*Attorney, Agent, or Firm*—Jeffry J. Grainger; Jens E. Hoekendijk; Michael J. Lynch

[57] ABSTRACT

An aortic occlusion catheter has a blood return lumen for returning oxygenated blood to a patient and an occluding member for occluding the patient's ascending aorta. The blood return lumen has openings on both sides of the occluding member for infusing oxygenated blood on both sides of the occluding member.

8 Claims, 6 Drawing Sheets

U.S. PATENT DOCUMENTS

| | | |
|---|---|---|
| 280,225 | 6/1883 | Noe . |
| 299,622 | 6/1884 | Chase . |
| 303,757 | 8/1884 | Sears et al. . |
| 1,282,881 | 10/1918 | Landis . |
| 2,029,236 | 1/1936 | Klophaus . |
| 2,308,484 | 1/1943 | Auzin et al. . |
| 2,531,730 | 11/1950 | Henderson . |
| 2,854,982 | 10/1958 | Pagano . |
| 3,326,648 | 6/1967 | Provisor . |
| 3,385,300 | 5/1968 | Holter . |
| 3,409,013 | 11/1968 | Berry . |
| 3,587,115 | 6/1971 | Shiley . |
| 3,635,223 | 1/1972 | Klieman . |
| 3,671,979 | 6/1972 | Moulopoulos . |
| 3,674,014 | 7/1972 | Tillander . |
| 3,692,018 | 9/1972 | Goetz et al. . |
| 3,755,823 | 9/1973 | Hancock . |
| 3,766,924 | 10/1973 | Pidgeon . |
| 3,769,960 | 11/1973 | Robinson . |
| 3,788,328 | 1/1974 | Alley et al. . |
| 3,833,003 | 9/1974 | Taricco . |
| 3,837,347 | 9/1974 | Tower . |
| 3,889,686 | 6/1975 | Duturbure . |
| 3,903,895 | 9/1975 | Alley et al. . |
| 3,915,171 | 10/1975 | Shermeta . |
| 3,963,028 | 6/1976 | Cooley et al. . |
| 3,970,090 | 7/1976 | Loiacono . |
| 3,983,879 | 10/1976 | Todd . |
| 4,000,739 | 1/1977 | Stevens . |
| 4,019,515 | 4/1977 | Kornblum et al. . |
| 4,029,104 | 6/1977 | Kerber . |
| 4,038,703 | 8/1977 | Bokros . |
| 4,056,854 | 11/1977 | Boretos et al. . |
| 4,106,129 | 8/1978 | Carpentier et al. . |
| 4,122,858 | 10/1978 | Schiff . |
| 4,154,227 | 5/1979 | Krause et al. . |
| 4,173,981 | 11/1979 | Mortensen et al. . |
| 4,204,328 | 5/1980 | Kutner . |
| 4,222,126 | 9/1980 | Boretos et al. . |
| 4,248,224 | 2/1981 | Jones . |
| 4,276,874 | 7/1981 | Wolvek et al. . |
| 4,284,073 | 8/1981 | Krause et al. . |
| 4,285,341 | 8/1981 | Pollack . |
| 4,287,892 | 9/1981 | Schiff . |
| 4,290,428 | 9/1981 | Durand et al. . |
| 4,297,749 | 11/1981 | Davis et al. . |
| 4,301,803 | 11/1981 | Handa et al. . |
| 4,304,239 | 12/1981 | Perlin . |
| 4,323,071 | 4/1982 | Simpson et al. . |
| 4,327,709 | 5/1982 | Hanson et al. . |
| 4,328,056 | 5/1982 | Snooks . |
| 4,343,048 | 8/1982 | Ross et al. . |
| 4,351,341 | 9/1982 | Goldberg et al. . |
| 4,405,313 | 9/1983 | Sisley et al. . |
| 4,411,055 | 10/1983 | Simpson et al. . |
| 4,413,989 | 11/1983 | Schjeldahl et al. . |
| 4,417,576 | 11/1983 | Baran . |
| 4,430,081 | 2/1984 | Timmermans . |
| 4,439,186 | 3/1984 | Kuhl . |
| 4,441,495 | 4/1984 | Hicswa . |
| 4,451,251 | 5/1984 | Osterholm . |
| 4,456,000 | 6/1984 | Schjeldahl et al. . |
| 4,459,977 | 7/1984 | Pizon . |
| 4,464,175 | 8/1984 | Altman et al. . |
| 4,493,697 | 1/1985 | Krause et al. . |
| 4,496,345 | 1/1985 | Hasson . |
| 4,497,325 | 2/1985 | Wedel . |
| 4,512,762 | 4/1985 | Spears . |
| 4,527,549 | 7/1985 | Gabbay . |
| 4,531,935 | 7/1985 | Berryessa . |
| 4,531,936 | 7/1985 | Gordon . |
| 4,535,757 | 8/1985 | Webster, Jr. . |
| 4,540,399 | 9/1985 | Litzie et al. . |
| 4,552,558 | 11/1985 | Muto . |
| 4,573,966 | 3/1986 | Weikl et al. . |
| 4,574,803 | 3/1986 | Storz . |
| 4,580,568 | 4/1986 | Gianturco . |
| 4,592,340 | 6/1986 | Boyles . |
| 4,596,552 | 6/1986 | DeVries . |
| 4,601,706 | 7/1986 | Aillon . |
| 4,601,713 | 7/1986 | Fuqua . |
| 4,610,661 | 9/1986 | Possis et al. . |
| 4,612,011 | 9/1986 | Kautzky . |
| 4,631,052 | 12/1986 | Kensey . |
| 4,639,252 | 1/1987 | Kelly et al. . |
| 4,648,384 | 3/1987 | Schmukler . |
| 4,664,125 | 5/1987 | Pinto . |
| 4,681,117 | 7/1987 | Brodman et al. . |
| 4,686,085 | 8/1987 | Osterholm . |
| 4,689,041 | 8/1987 | Corday et al. . |
| 4,692,148 | 9/1987 | Kantrowitz et al. . |
| 4,697,574 | 10/1987 | Karcher et al. . |
| 4,705,507 | 11/1987 | Boyles . |
| 4,714,460 | 12/1987 | Calderon . |
| 4,721,109 | 1/1988 | Healey . |
| 4,722,347 | 2/1988 | Abrams et al. . |
| 4,723,550 | 2/1988 | Bales et al. . |
| 4,723,936 | 2/1988 | Buchbinder et al. . |
| 4,733,665 | 3/1988 | Palmaz . |
| 4,741,328 | 5/1988 | Gabbay . |
| 4,751,924 | 6/1988 | Hammerschmidt et al. . |
| 4,753,637 | 6/1988 | Horneffer . |
| 4,767,409 | 8/1988 | Brooks . |
| 4,770,652 | 9/1988 | Mahurkar . |
| 4,771,777 | 9/1988 | Horzewski et al. . |
| 4,777,951 | 10/1988 | Cribier et al. . |
| 4,785,795 | 11/1988 | Singh . |
| 4,787,899 | 11/1988 | Lazarus . |
| 4,787,901 | 11/1988 | Baykut . |
| 4,790,825 | 12/1988 | Bernstein et al. . |
| 4,794,928 | 1/1989 | Kletschka . |
| 4,796,629 | 1/1989 | Grayzel . |
| 4,798,588 | 1/1989 | Aillon . |
| 4,804,358 | 2/1989 | Karcher et al. . |
| 4,804,365 | 2/1989 | Litzie et al. . |
| 4,808,165 | 2/1989 | Carr . |
| 4,809,681 | 3/1989 | Kantrowitz et al. . |
| 4,811,737 | 3/1989 | Rydell . |
| 4,821,722 | 4/1989 | Miller et al. . |
| 4,830,849 | 5/1989 | Osterholm . |
| 4,848,344 | 7/1989 | Sos et al. . |
| 4,850,969 | 7/1989 | Jackson . |
| 4,856,516 | 8/1989 | Hillstead . |
| 4,865,581 | 9/1989 | Lundquist et al. . |
| 4,877,031 | 10/1989 | Conway et al. . |
| 4,877,035 | 10/1989 | Bogen et al. . |
| 4,878,495 | 11/1989 | Grayzel . |
| 4,883,458 | 11/1989 | Shiber . |
| 4,886,507 | 12/1989 | Patton et al. . |
| 4,889,137 | 12/1989 | Kolobow . |
| 4,898,168 | 2/1990 | Yule . |
| 4,902,272 | 2/1990 | Milder et al. . |
| 4,902,273 | 2/1990 | Choy et al. . |
| 4,917,667 | 4/1990 | Jackson . |
| 4,923,450 | 5/1990 | Maeda et al. . |
| 4,927,412 | 5/1990 | Menasche . |
| 4,934,996 | 6/1990 | Mohl et al. . |
| 4,943,275 | 7/1990 | Stricker . |
| 4,943,277 | 7/1990 | Bolling . |
| 4,960,412 | 10/1990 | Fink . |
| 4,966,604 | 10/1990 | Reiss . |
| 4,969,470 | 11/1990 | Mohl et al. . |

| | | |
|---|---|---|
| 4,979,939 | 12/1990 | Shiber . |
| 4,985,014 | 1/1991 | Orejola . |
| 4,986,830 | 1/1991 | Owens et al. . |
| 4,990,143 | 2/1991 | Sheridan . |
| 4,994,032 | 2/1991 | Sugiyama et al. . |
| 4,994,033 | 2/1991 | Shockey et al. . |
| 5,007,896 | 4/1991 | Shiber . |
| 5,009,636 | 4/1991 | Wortley et al. . |
| 5,011,468 | 4/1991 | Lundquist et al. . |
| 5,011,469 | 4/1991 | Buckberg et al. . |
| 5,011,488 | 4/1991 | Ginsburg . |
| 5,013,296 | 5/1991 | Buckberg et al. . |
| 5,021,044 | 6/1991 | Sharkaway . |
| 5,021,045 | 6/1991 | Buckberg et al. . |
| 5,024,668 | 6/1991 | Peters et al. . |
| 5,026,366 | 6/1991 | Leckrone . |
| 5,032,128 | 7/1991 | Alonso . |
| 5,033,998 | 7/1991 | Corday et al. . |
| 5,037,434 | 8/1991 | Lane . |
| 5,041,093 | 8/1991 | Chu . |
| 5,041,098 | 8/1991 | Loiterman et al. . |
| 5,047,041 | 9/1991 | Samuels . |
| 5,049,132 | 9/1991 | Shaffer et al. . |
| 5,053,008 | 10/1991 | Bajaj . |
| 5,059,167 | 10/1991 | Lundquist et al. . |
| 5,069,661 | 12/1991 | Trudell . |
| 5,069,662 | 12/1991 | Bodden . |
| 5,080,660 | 1/1992 | Buelna . |
| 5,089,015 | 2/1992 | Ross . |
| 5,106,368 | 4/1992 | Uldall et al. . |
| 5,109,859 | 5/1992 | Jenkins . |
| 5,112,305 | 5/1992 | Barath et al. . |
| 5,116,305 | 5/1992 | Milder et al. . |
| 5,125,903 | 6/1992 | McLaughlin et al. . |
| 5,152,771 | 10/1992 | Sabbaghian et al. . |
| 5,163,953 | 11/1992 | Vince . |
| 5,167,628 | 12/1992 | Boyles . |
| 5,171,232 | 12/1992 | Castillo et al. . |
| 5,176,619 | 1/1993 | Segalowitz . |
| 5,181,518 | 1/1993 | McDonagh et al. . |
| 5,186,713 | 2/1993 | Raible . |
| 5,195,942 | 3/1993 | Weil et al. . |
| 5,197,952 | 3/1993 | Marcadis et al. . |
| 5,216,032 | 6/1993 | Manning . |
| 5,219,326 | 6/1993 | Hattler . |
| 5,226,427 | 7/1993 | Buckberg et al. . |
| 5,236,413 | 8/1993 | Feiring . |
| 5,246,007 | 9/1993 | Frisbie et al. . |
| 5,250,038 | 10/1993 | Melker et al. . |
| 5,250,069 | 10/1993 | Nobuyoshi et al. . |
| 5,254,089 | 10/1993 | Wang . |
| 5,254,097 | 10/1993 | Schock et al. . |
| 5,270,005 | 12/1993 | Raible . |
| 5,275,622 | 1/1994 | Lazarus et al. . |
| 5,290,231 | 3/1994 | Marcadis et al. . |
| 5,295,958 | 3/1994 | Shturman . |
| 5,308,320 | 5/1994 | Safar et al. . |
| 5,312,344 | 5/1994 | Grinfeld et al. . |
| 5,314,418 | 5/1994 | Takano et al. . |
| 5,322,500 | 6/1994 | Rickerd . |
| 5,322,509 | 6/1994 | Rickerd . |
| 5,324,260 | 6/1994 | O'Neill et al. . |
| 5,330,451 | 7/1994 | Gabbay . |
| 5,332,402 | 7/1994 | Teitelbaum . |
| 5,334,142 | 8/1994 | Paradis . |
| 5,370,618 | 12/1994 | Leonhardt . |
| 5,370,640 | 12/1994 | Kolff . |
| 5,374,245 | 12/1994 | Mahurkar . |
| 5,380,282 | 1/1995 | Burns . |
| 5,382,239 | 1/1995 | Orr et al. . |
| 5,383,854 | 1/1995 | Safar et al. . |
| 5,385,548 | 1/1995 | Williams et al. . |
| 5,395,330 | 3/1995 | Marcadis et al. . |
| 5,395,331 | 3/1995 | O'Neill et al. . |
| 5,397,306 | 3/1995 | Nobuyoshi et al. . |
| 5,397,351 | 3/1995 | Pavcnik et al. . |
| 5,411,027 | 5/1995 | Wiklund et al. . |
| 5,411,479 | 5/1995 | Bodden . |
| 5,411,552 | 5/1995 | Andersen et al. . |
| 5,421,825 | 6/1995 | Farcot . |
| 5,425,708 | 6/1995 | Nasu . |
| 5,428,070 | 6/1995 | Cooke et al. . |
| 5,433,446 | 7/1995 | Shturman . |
| 5,433,700 | 7/1995 | Peters . |
| 5,437,633 | 8/1995 | Manning . |
| 5,439,443 | 8/1995 | Miyata et al. . |
| 5,451,207 | 9/1995 | Yock . |
| 5,456,665 | 10/1995 | Postell et al. . |
| 5,458,574 | 10/1995 | Machold et al. . |
| 5,478,309 | 12/1995 | Sweezer et al. . |
| 5,480,424 | 1/1996 | Cox . |
| 5,487,730 | 1/1996 | Marcadis et al. . |
| 5,499,996 | 3/1996 | Hill . |
| 5,505,698 | 4/1996 | Booth et al. . |
| 5,509,897 | 4/1996 | Twardowski et al. . |
| 5,525,388 | 6/1996 | Wand et al. . |
| 5,527,292 | 6/1996 | Adams et al. . |
| 5,533,957 | 7/1996 | Aldea . |
| 5,562,606 | 10/1996 | Huybregts . |
| 5,578,010 | 11/1996 | Ashby . |
| 5,584,803 | 12/1996 | Stevens . |
| 5,591,129 | 1/1997 | Shoup et al. . |
| 5,595,181 | 1/1997 | Hubbard . |
| 5,597,377 | 1/1997 | Aldea et al. . |
| 5,599,329 | 2/1997 | Gabbay . |

OTHER PUBLICATIONS

Douville et al., "Retrograde Versus Antegrade Cardioplegia: Impact on Right Ventricular Function," *Ann Thorac Surg*, 1992; 54:56–61.

Drinkwater et al., "The Use of Combined Antegrade–Retrograde Infusion of Blood Cardioplegic Solution in Pediatric Patients Undergoing Heart Operations," *Thorac and Cardiovascular Surg*. 1992; 104(5):1349–1355.

Elecath, "Bain Coronary Sinus Flow Catheter for Jugular Entry," Catalog No. 75–2337, 1994.

Erath and Stoney, "Balloon Catheter Occlusion of the Ascending Aorta," *Ann Thorac Surg*, 1983;35:560–561.

Farcot et al., "New Catheter–Pump System for Diastolic Synchronized Coronary Sinus Retroperfusion (D.S.R.)," *Med Prog Technol*, 1980; 8(1):29–37.

Farcot et al., "Synchronized Retroperfusion of Coronary Veins for Circulatory Support of Jeopardized Ischemic Myocardium," *Am J Cardiol*, 1978; 41:1101–1201.

Foster and Threlkel, "Proximal Control of Aorta with a Balloon Catheter," *Surg Gynecology & Obstetrics*, 1971, pp. 693–694.

Gundry et al., "A Comparison of Retrograde of Cardioplegia Versus Antegrade Cardioplegia in the Presence of Coronary Artery Obstruction," *Ann Thorac Sug*, 1984; 38(2):124–127.

Gundry, "Modification of Myocardial Ischemic in Normal and Hypertrophied Hearts Utilizing Diastolic Retroperfusion of the Coronary Veins," *J Thorac Cardiovasc Sug*, 1982; 83:659–669.

Haendchen et al., "Prevention of Ischemic Injury and Early Reperfusion Derangements by Hypothermic Retroperfusion," *J Am Coll Cardiol*, 1983; 1(4):1067–1080.

Hammond et al., "Retrograde Coronary Sinus Perfusion: A Method of Myocardial Protection in the Dog During Left Coronary Artery Occlusion," *Ann Surg*, 1967; 166(1):139–147.

Ishizaka, "Myocardial Protection by Retrograde Cardiac Perfusion with Cold Medified Krebs Solution through Coronary Sinus During Complete Ischemic Arrest for 120 Minutes," *J Jpn Assn Thorac Surg*, 1977;25(12);:1592–1601.

Kalmbach et al., "Cardioplegia Delivery by Combined Aoratic Root and Coronary Sinus Perfusion," *Ann Thorac Sug*. 1989;47:316–317.

Leggett et al., "Fiberoptic Cardioscopy Under Cardiopulmonary Bypass: Potential for Cardioscopy Surgery?" *Ann Thorac Sug*, 1994;58:222–225.

Lust et al., "Improved Protection of Chronically Inflow–limited Myocardium with Retrograde Coronary Sinus Cardioplegia," *Circulation III*, 1988;78(5):217–223.

Markov et al., "Reversal of Acute Myocardial Ischemia in Closed Chest Animals by Retrograde Perfusion of the Coronary Sinus with Arterial Blood," *Acta Cardiologica*, 1976; XXXI(3): 185–199.

Medex, Inc., MX220 Single Tuohy–Borst Adaptor: Instructions for Use, 1992.

Medi–Tech, Boston Scientific Corporation, "Occlusion Balloon Catheters: Instructions for Use," Rev. Jun. 1991.

Medtronic Bio–Medicus, Inc., "Bio—Medicus Cannula Introducer Instructions for Use Manual," PN 85146–Rev. C(Jul./1991).

Medtronic Bio–Medicus Femoral Cannulae advertisement, ©1991.

Medtronic Bio–Medicus Percutaneous Cannula Kits advertisements, © 1991.

Meerbaum et al., "Diastolic Retroperfusion of Acutely Ischemic Myocardium," *Am J Cardiol*, 1976; 37:588–598.

Meerbaum et al., "Hypothermic Coronary Venous Phased Retroperfusion: A Closed–Chest Treatment of Acute Regional Myocardial Ischemia," *Circulation*, 1982; 65(7): 1435–1445.

Meerbaum et al., "Retrograde Lysis of Coronary Artery Thrombus by Coronary Venouse Strepokinase Administration," *J Am Coll Cardiol*, 1983; 1(5):1262–1267.

Menasche et al., "Cardioplegia by Way of the coronary Sinus for Valvular and Coronary Surgery," *Jacc*, 1991; 18(2):628–636.

Menasche et al., "Retrograde Cardioplegia through the Coronary Sinus," *Ann Thorac Surg*, 1987; 44:214–216.

Menasche et al., "Retrograde Warm Blood Cardioplegia Preserves Hypertrophied Myocardium: A Clinical Study," *Ann Thorac Surg*, 1994; 57:1429–1435.

Pilling Surgical Instruments, Vascular Clamps –Cooley Brochure, p. 385 (no date).

Razi, D..M., "The Challenge of Calcific Aortitis," *J Cardiac Surg*, 1993; 8:102–107.

Research Medical, Inc., Cardioplegia Products, Product Catalog 1995.

Research Medical, Inc., Fem Flex Femoral Percutaneous Cannulae, Advertisement, *Ann Thorac Surg*, Jan. 1995, p. A38.

Ropchan et al., "Salvage of Ischemic Myocardium by Non-synchronized Retroperfusion in the Pig," *The Journal of Thoracic and Cardiovascular Surgery*, Sep. 1992, vol. 104, No. 3, pp. 619–625.

Sabiston, D.C., Textbook of Surgery, 10[th]Ed., 1972, pp. 2021–2023, 2114–2121.

Shumway, "Forward Versus Retrograde Coronary Perfusion for Direct Vision Surgery of Acquired Aortic Valvular Disease," *J Thoracic and Cardiovasc Surg*, 1959; 75–80.

Uchida et al., "Percutaneous Cariomyotomy ad Valvulotomy with Angioscopic Guidance," *American Heart Journal*, 1991;121(4,part I): 1221–1224.

Uchida et al., "Percutaneous Fiberoptic Angioscopy of the Cardiac Valves," *Am Heart J*, 1991; 121(6, part I):1791–1798.

METHODS AND DEVICES FOR OCCLUDING A PATIENT'S ASCENDING AORTA

BACKGROUND OF THE INVENTION

The present invention is directed to methods and devices for occluding a patient's ascending aorta and returning oxygenated blood to the patient when the patient is supported by a bypass system. The invention is particularly useful when performing surgery on the heart and great vessels.

In conventional open heart surgery, the patient's heart is accessed through a large opening in the patient's chest, such as a median sternotomy. With the patient's heart exposed, various catheters, cannulae and clamps are applied directly to the patient's heart and great vessels. Blood is withdrawn from the patient through a venous cannula and returned to the patient through an arterial return cannula which is typically inserted through a pursestring suture in the ascending aorta. The heart is arrested by infusing a cardioplegic fluid into the ascending aorta with a needle. The ascending aorta is typically occluded with an external cross-clamp around the ascending aorta to isolate the coronary arteries from the remainder of the arterial system.

Recent developments in cardiac surgery have provided cannulae and catheters for occluding a patient's ascending aorta, returning oxygenated blood to the patient, and delivering cardioplegic fluid to the patient without requiring direct access to the patient's heart. Such systems are described in U.S. Pat. Nos. 5,584,803, 5,478,309 and Re. 35,352. The devices and methods described in these patents enable surgeons to perform various procedures on the patient's heart and great vessels, such as bypass grafting and valve replacements, without requiring a large opening in the patient's chest. Such procedures reduce the pain and trauma suffered by the patient as compared to traditional open-heart procedures.

Another advantage of the systems described in U.S. Pat. Nos. 5,584,803, 5,478,309 and Re. 35,352 is that occlusion of the aorta is accomplished with a balloon positioned in the aorta rather than an external clamp around the aorta. Use of a balloon to occlude the ascending aorta may reduce the amount of emboli released into the bloodstream as compared to external cross-clamps thereby reducing stroke incidents.

Although the systems described above enable a wide range of surgical procedures on a stopped heart, positioning of the aortic occlusion balloon is often challenging since the balloon must be positioned in a relatively small space between the aortic valve and brachiocephalic artery. Inadvertent occlusion of the brachiocephalic artery is dangerous since the right carotid artery, which branches off the brachiocephalic artery and provides blood to the patient's brain, would also not receive oxygenated blood. Positioning of the balloon is particularly challenging when performing aortic valve procedures since the balloon must be positioned far enough from the aortic valve to permit the surgeon to perform the procedure on the aortic valve without interference from the balloon.

Thus, an object of the present invention is to provide an aortic occlusion catheter having an occluding member which may be easily positioned within a patient's ascending aorta.

SUMMARY OF THE INVENTION

The present invention provides an aortic occlusion catheter and method of occluding a patient's ascending aorta and delivering oxygenated blood to the patient from a bypass system. The aortic occlusion catheter is inserted through a penetration in the patient's arterial system and passed through the junction between the brachiocephalic artery and ascending aorta. In a preferred embodiment, the aortic occlusion catheter preferably enters the patient's arterial system through a penetration in the axillary or subclavian artery.

The aortic occlusion catheter has an occluding member which is positioned in the ascending aorta and expanded to occlude the patient's ascending aorta thereby isolating the coronary arteries from the rest of the patient's arterial system. The occluding member, which is preferably a balloon, is preferably attached to the catheter shaft along a portion between proximal and distal ends of the occluding member. When the occluding member is expanded, the occluding member expands toward one side of the shaft. In a preferred embodiment, the expanding side of the occluding member is positioned to expand toward the aortic valve.

The aortic occlusion catheter also has a blood flow lumen having first and second openings for returning oxygenated blood to the patient. The first and second openings are on opposite sides of the occluding member so that oxygenated blood is delivered to both sides of the occluding member. One of the openings provides oxygenated blood to arteries superior to the junction between the brachiocephalic artery and the aortic arch while the other opening provides oxygenated blood to the rest of the body. An advantage of providing openings on both sides of the occluding member is that occlusion of the brachiocephalic artery does not pose a risk to the patient since oxygenated blood is delivered to both sides of the occluding member. Another advantage of the aortic occlusion catheter is that the occluding member is easily positioned far from the aortic valve thereby maximizing the working space for performing aortic valve procedures.

The aortic occlusion catheter also preferably includes two pressure lumens for measuring pressure on both sides of the occluding member. Although two pressure lumens are preferred, only one pressure lumen may be necessary. The pressure lumens are coupled to a pressure monitor for measuring the blood pressure on both sides of the occluding member. The pressure monitor is used to prevent excessively high or low blood pressures and, in particular, excessively high blood pressure in the carotid arteries.

These and other features will become apparent from the following description of the preferred embodiment.

DESCRIPTION OF THE PREFERRED EMBODIMENTS

Figure 1:
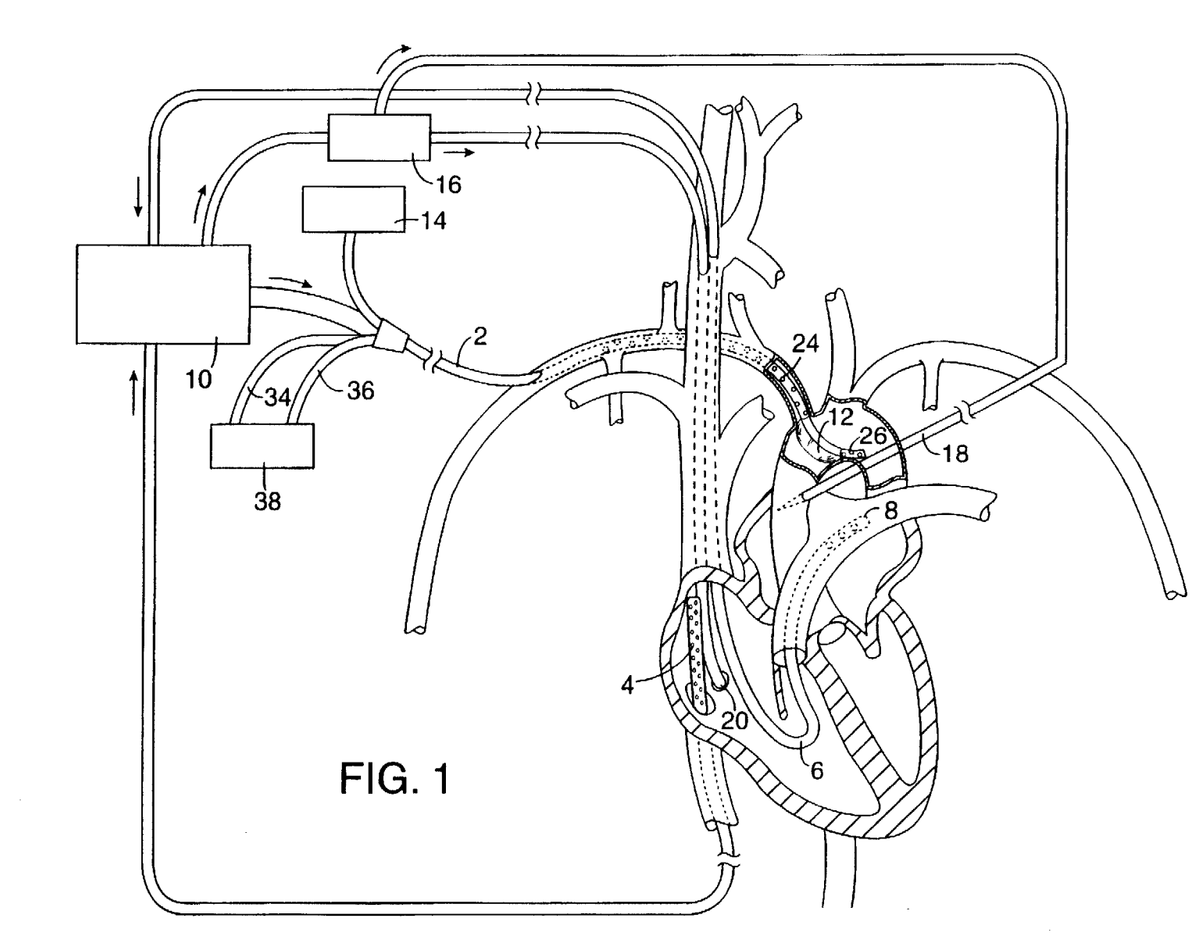
FIG. 1 is a partial cross-sectional view of a patient's heart and vascular system which illustrates an aortic occlusion catheter of the present invention together with a bypass system.

Referring to FIG. 1, a system for arresting a patient's heart and maintaining circulation of oxygenated blood through the patient is shown. The system is shown for the purposes of illustrating an aortic occlusion catheter 2 in accordance with the present invention and other systems, catheters, cannulae and the like may be used with the invention without departing from the scope of the invention.

Blood is withdrawn from the patient through a venous cannula 4 which is inserted into the patient's vascular system at any suitable location. FIG. 1 illustrates the venous cannula 4 passing through the femoral vein and into the patient's right atrium. Blood is also withdrawn from the patient through a venting catheter 6 which vents the patient's heart through the pulmonary vasculature. The venting catheter 6 extends through the internal jugular vein and tricuspid and pulmonary valves so that a distal end 8 is in the pulmonary artery. Although it is preferred to provide the venting catheter 6, venting of the heart may also be accomplished with any other device such as a needle penetrating the pulmonary artery.

Blood withdrawn through the venous cannula 4 and venting catheter 6 is directed to a bypass system 10 which preferably includes a pump for pumping oxygenated blood through the patient. The bypass system 10 may also include one or more of the following: a heat exchanger, oxygenator, filter, bubble trap, and cardiotomy reservoir. The bypass system 10 preferably includes an external oxygenator, however, the patient's own lungs may also be used to oxygenate the blood.

After the blood passes through the bypass system 10, oxygenated blood is returned to the patient from the bypass system 10 through the aortic occlusion catheter 2 which is described in greater detail below. The aortic occlusion catheter 2 has an occluding member 12, which is preferably a balloon, for occluding the patient's ascending aorta. Occlusion of the ascending aorta isolates the coronary arteries from the remainder of the arterial system to prevent the heart from receiving oxygenated blood and starting prematurely before completion of the surgical procedure. A source of inflation fluid 14, which is preferably a syringe filled with saline solution, is used to inflate the occluding member 12.

The patient's heart may be arrested using any method and a preferred method is to use a cardioplegic fluid. Cardioplegic fluid may be administered antegrade or retrograde through the coronary sinus. The system shown in FIG. 1 includes both antegrade and retrograde perfusion, however, only one type of perfusion may be necessary. The cardioplegic fluid may be any type of cardioplegic fluid and a preferred cardioplegic fluid is blood cardioplegia which is a mixture of crystalloid cardioplegia and blood. A source of cardioplegic fluid 16 draws blood from the bypass system 10 for mixing with a cardioplegic agent to form the cardioplegic fluid. Cardioplegic fluid is introduced antegrade with a needle 18 and retrograde with a coronary sinus catheter 20. The coronary sinus catheter 20 passes through the internal jugular vein, into the right atrium and into the coronary sinus 20. The coronary sinus catheter 20 preferably has a balloon (not shown) for occluding the coronary sinus. Although it is preferred to endovascularly advance the coronary sinus catheter through a peripheral vein, the coronary sinus catheter 20 may also simply pass through an opening in the right atrium.

Figure 2:
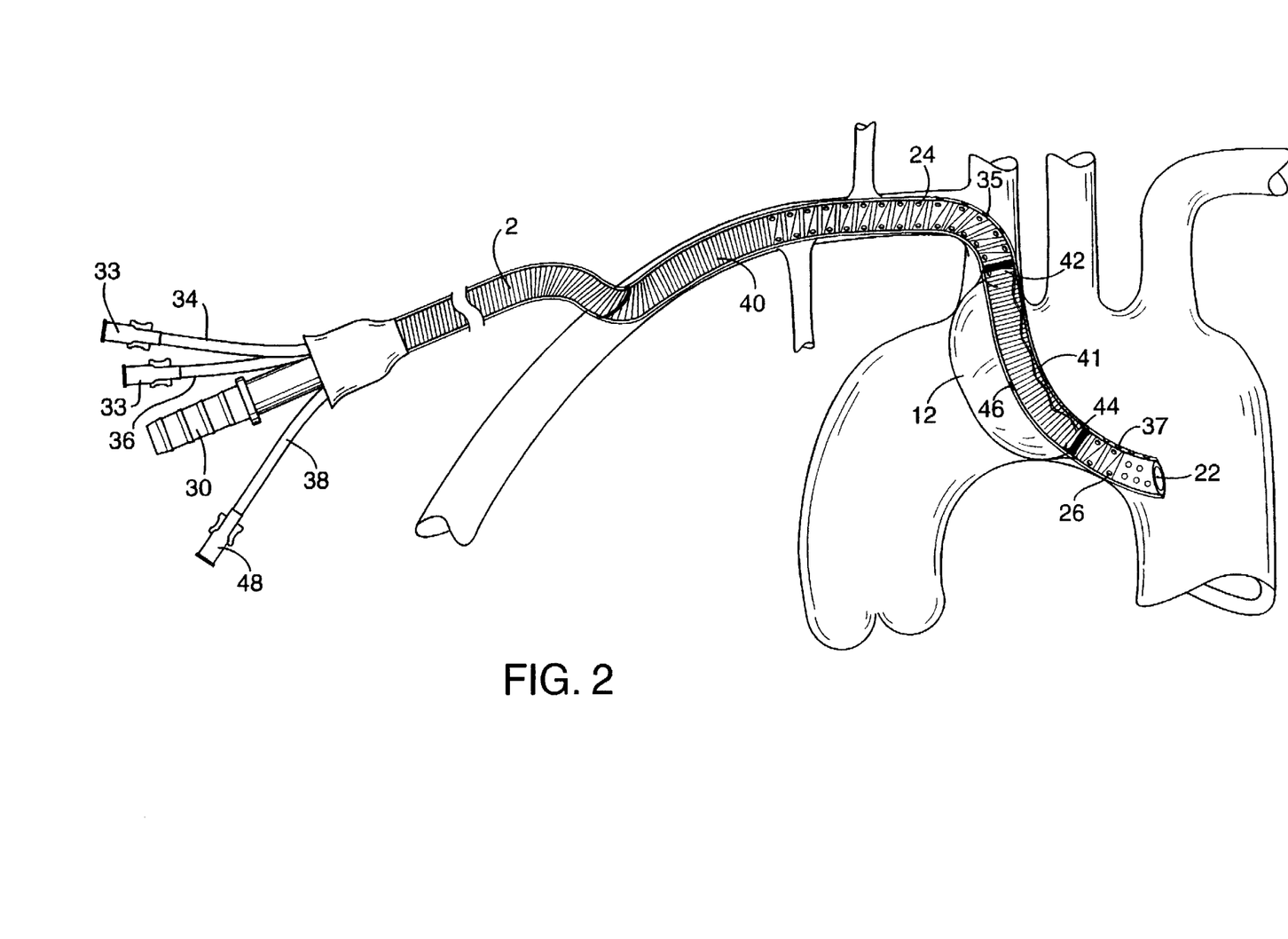
FIG. 2 is an enlarged view of the aortic occlusion catheter of FIG. 1.
Figure 3:
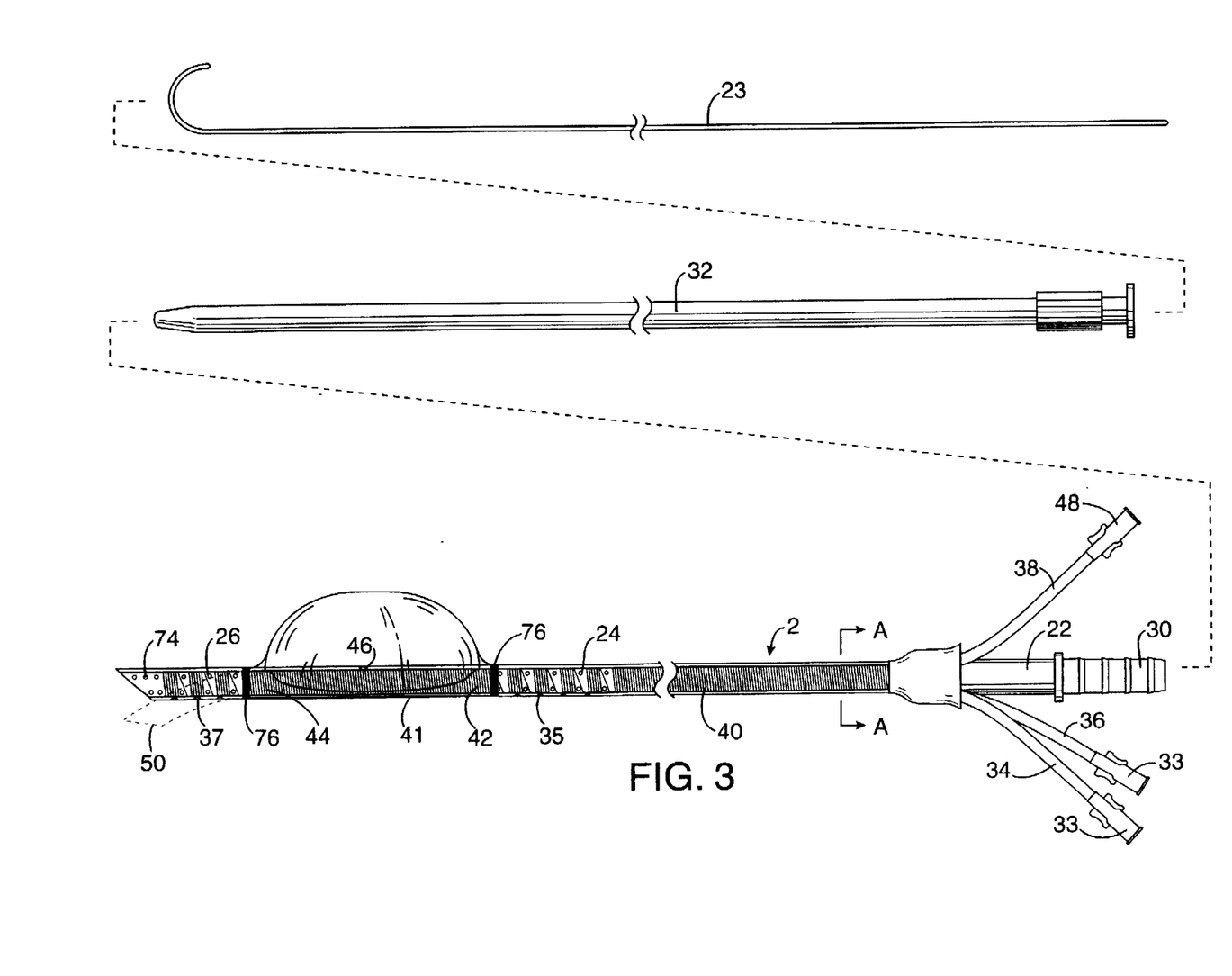
FIG. 3 is a side view of the aortic occlusion catheter of FIGS. 1 and 2.

Referring now to FIGS. 1-3, the aortic occlusion catheter 2 has a blood return lumen 22 for returning oxygenated blood to the patient from the bypass system 10. The blood return lumen 22 has proximal openings 24 and distal openings 26 for infusing oxygenated blood from the bypass system 10 on both sides of the occluding member 12. Delivery of oxygenated blood through the proximal openings 24 provides oxygenated blood to arteries downstream of the brachiocephalic artery such as the axillary, subclavian and carotid arteries. Delivery of oxygenated blood through the distal openings 26, which includes the open end 28 of the catheter 2, provides oxygenated blood to the rest of the body. The proximal openings 24 preferably have a diameter of between 0.02 and 0.2 inch and more preferably 0.04 inch and a preferred number of proximal openings 24 is between 3 and 60. The total area of the proximal openings 24 is preferably about 5% to 30% and more, preferably about 10% of the area of the distal openings 26 so that more oxygenated blood passes through the distal openings 26 since a larger portion of the patient's arterial system is distal to the occluding member 12. The blood return lumen 22 terminates at a conventional barbed connection 30 suitable for connection to the bypass system 10. The blood return lumen 22 is preferably coated with a conventional athrombogenic coating such as benzalkonium heparin to minimize damage to the blood. The outside of the catheter 2 may also be coated with a lubricious coating to facilitate introduction of the catheter 2 into the patient. Any suitable coating may be used and a preferred coating is polyvinyl pyrrolidone.

Still referring to FIGS. 1-3, the aortic occlusion catheter 2 preferably enters the patient's aortic arch from the brachiocephalic artery and enters through a penetration in the subclavian, axillary, or brachial arteries. FIG. 1 shows the aortic occlusion catheter 2 passing through a penetration in the axillary artery and passing through the subclavian and brachiocephalic arteries. When inserting the aortic occlusion catheter 2 through the penetration and advancing the catheter 2 through the patient's arteries, an obturator 32 is positioned in the blood return lumen 22 to provide an atraumatic distal end. Using fluoroscopy, a guidewire 23 is first passed through the artery. The aortic occlusion catheter 2 and accompanying obturator 32 are then passed together over the guidewire 23 to position the catheter as shown in FIG. 2. Once the catheter 2 is in position, the obturator 32 and guidewire 23 are removed. The catheter 2 is then primed to remove all air by permitting blood to flow through the catheter 2 and the catheter 2 is then connected to the bypass system 1.

As shown in FIGS. 1 and 2, the aortic occlusion catheter 2 is positioned to occlude or partially occlude the brachiocephalic artery. This would normally present a dangerous condition, however, the proximal openings 24 provide oxygenated blood to arteries downstream of the brachiocephalic artery such as the subclavian, carotid and axillary arteries so that even complete occlusion of the brachiocephalic artery is not a problem. Thus, an advantage of the aortic occlusion catheter 2 of the present invention is that the occluding member 12 is readily positioned away from the patient's aortic valve so that contact with the aortic valve is not a problem while also eliminating the risk that occlusion of the brachiocephalic artery will cut off blood to the carotid artery. The aortic occlusion catheter 2 is particularly useful when performing aortic valve procedures since the occluding member 12 is positioned far from the aortic valve.

Referring to FIGS. 1–4, the aortic occlusion catheter 2 has first and second pressure lumens 34, 36 coupled to a pressure monitor 38 for monitoring pressures proximal and distal to the occluding member 12. The first and second pressure lumens 34, 36 have first and second pressure ports, 35, 37, respectively. Although it is preferred to provide the pressure lumens 34, 36, pressure sensing may be accomplished by any other method such as with pressure transducers. The pressure monitor 38 is used to prevent excessively high or low blood pressure when delivering blood through the proximal and distal openings 24, 26. If, for example, the distal openings 26 are occluded or obstructed, all of the blood would be forced through the proximal openings 24 which may create undesirably high pressures in the brachiocephalic and carotid arteries. A pressure relief valve (not shown) may be provided to prevent excessive pressures when delivering blood to the patient. Alternatively, a pressure sensor may be coupled to the bypass system 10 so that the delivery of oxygenated blood is regulated to prevent excessive pressures. Although it is preferred to provide both the first and second pressure lumens, 34, 36, only one of the lumens 34, 36 may also be provided such as only the first lumen 34. The pressure lumens 34, 36 have connectors 33 suitable for connection to the pressure monitor 38.

Figure 4:
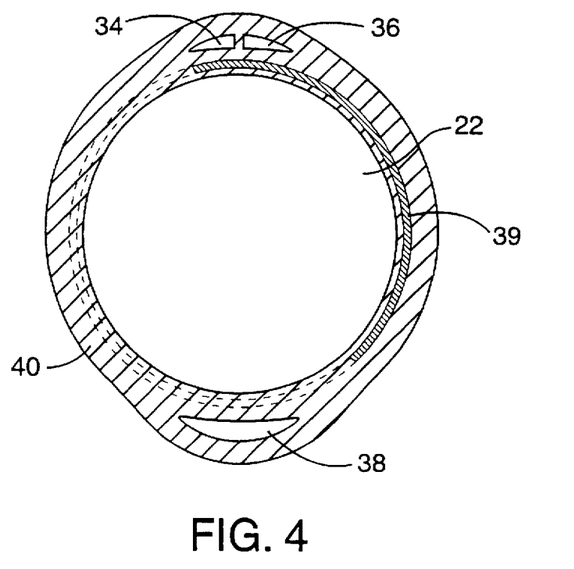
FIG. 4 is a cross-sectional view of the aortic occlusion catheter at line A—A of FIG. 3.
Figure 5:
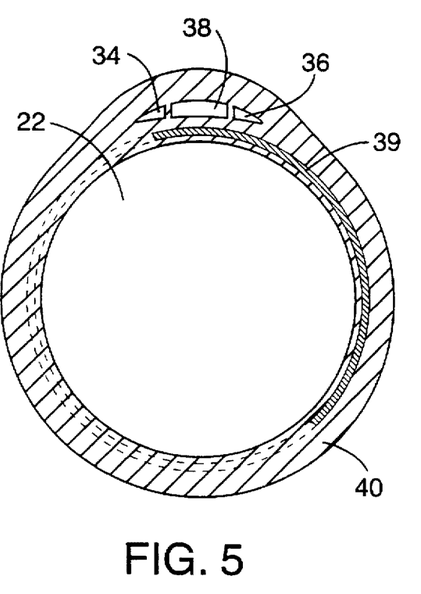
FIG. 5 is a cross-sectional view of another aortic occlusion catheter.
Figure 6:
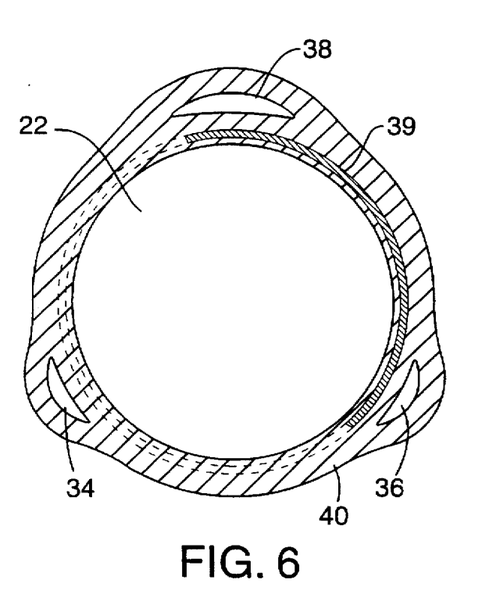
FIG. 6 is a cross-sectional view of yet another aortic occlusion catheter.

Referring to FIG. 4, a cross-sectional view of the aortic occlusion catheter 2 is shown. The pressure lumens 34, 36 are positioned opposite an inflation lumen 38 which is used to inflate the occluding member 12. The aortic occlusion catheter 2 is preferably reinforced with a wire 39 which is wound helically around catheter shaft 40. FIG. 5 shows an alternative construction in which the pressure lumens 34, 36 and inflation lumen 38 are positioned adjacent one another while FIG. 6 shows the pressure lumens 34, 36 and inflation lumen 38 spaced around the periphery of the aortic occlusion catheter 2. The method of forming the catheter 2 is described in greater detail below.

Referring again to FIGS. 1–3, the occluding member 12 is preferably an inflatable balloon which may be made of any suitable elastic or inelastic material and a preferred material is polyurethane. The occluding member 12 is preferably bonded to the shaft 40 along a side 41 extending between proximal and distal ends 42, 44 of the occluding member 12. The resulting occluding member 12 expands toward one side of the shaft 40 in the manner shown in FIGS. 1–3. Although it is preferred to bond the side 41 of the occluding member 12 to the shaft 40, the occluding member 12 may also be bonded to the shaft 40 only at the proximal and distal ends 42, 44 so that the occluding member 12 expands in all directions around the shaft 40. The inflation lumen 38, which has an inflation opening 46 for inflating the occluding member 12, has a connector 48 suitable for connection to the source of inflation fluid 14 for inflating the occluding member 12.

Referring to FIG. 2 and FIG. 4, the shaft 40 is preferably reinforced with the wire 39. Although it is preferred to provide a wire-reinforced construction for the shaft 40, the shaft 40 may have any other suitable construction such as an extrusion. The catheter 2 is preferably very flexible with the preferred shape being substantially straight when in an unbiased condition. Alternatively, the distal end of the catheter 2 may be slightly curved in the manner shown at dotted line 50 in FIG. 3.

The method of constructing the wire-reinforced shaft 40 is now described with reference to FIGS. 7–10. The method begins with construction of a reinforced tube 52. A first tube 54 is mounted on a mandrel (not shown) and the wire 39 is wrapped in a helical fashion around the first tube 54 in the manner shown in the longitudinal cross-section of FIGS. 7 and 9. The wire 39 is preferably a stainless steel wire having a diameter of between 0.001 and 0.015 inch and more preferably 0.007 inch. A second tube 56 is then positioned over the wire 39 and the first and second tubes 54, 56 are encased in a heat shrink tube (not shown) and heated so that the first and second tubes 54, 56 and wire 39 form the reinforced tube 52 shown in FIGS. 8 and 10, respectively. The first and second tubes 54, 56 preferably have a thickness of between 0.001 and 0.010 inch and more preferably 0.003 inch. The first and second tubes 54, 56 may be made of any suitable material and a preferred material is polyurethane.

Figure 7:
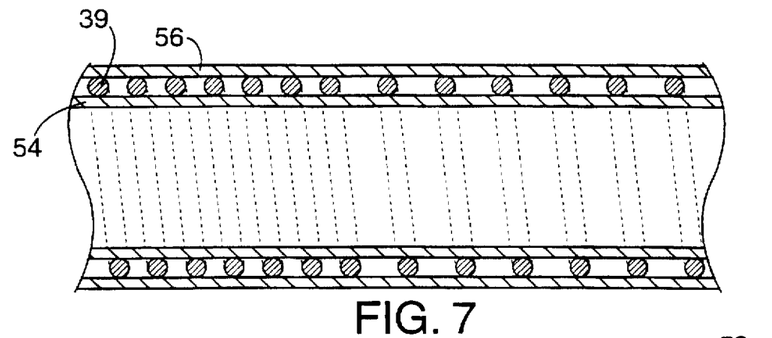
FIG. 7 is a longitudinal cross-sectional view illustrating a method of forming a wire-reinforced blood flow lumen.
Figure 8:
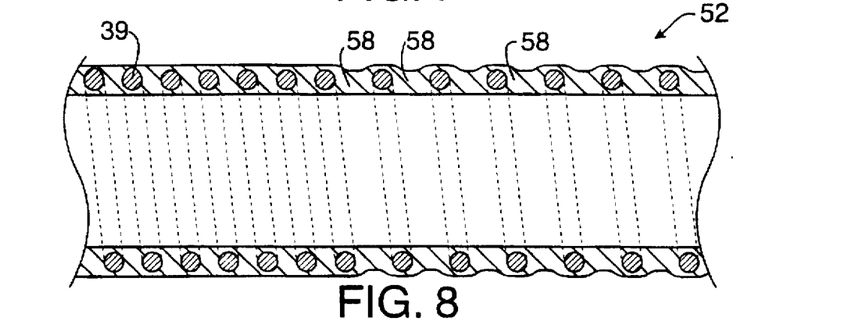
FIG. 8 is a longitudinal cross-sectional view of the structure of FIG. 7 after heating.
Figure 9:
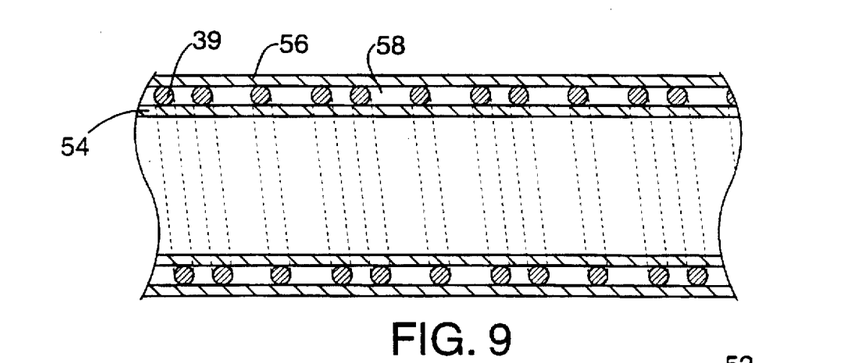
FIG. 9 is a longitudinal cross-sectional view illustrating a method of forming a second wire-reinforced blood flow lumen.
Figure 10:
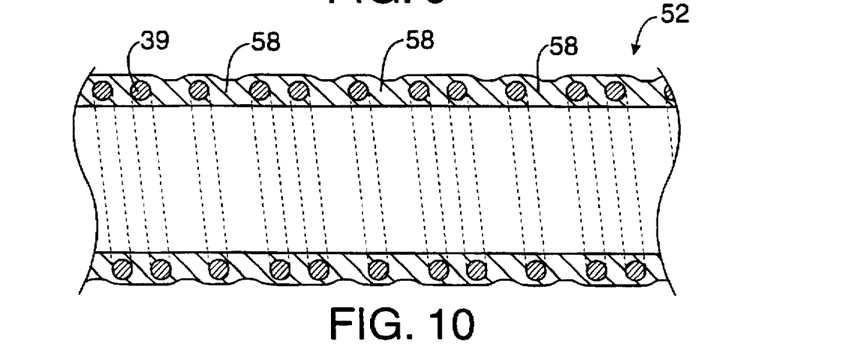
FIG. 10 is a longitudinal cross-sectional view of the structure of FIG. 9 after heating.

The wire 39 is preferably wrapped around the second tube 56 with a larger spacing around portions 58 of the shaft 40 where the proximal and distal openings 24, 26 will be formed so that the proximal and distal openings 24, 26 may be formed without cutting through the wire 39. FIGS. 7 and 8 illustrate a uniform spacing of about 0.040 inch between adjacent portions of the wire 39 at the portions 58 where the proximal and distal openings 24, 26 will be formed. FIGS. 9 and 10 show a construction having alternating small and large spacing with the proximal and distal openings 24, 26 being formed in the portions 58 having the large spacing. Yet another method is to provide a uniform spacing throughout the shaft 40 with the spacing being large enough to permit forming the proximal and distal openings 24, 26 without cutting through the wire 39. FIGS. 8 and 10 illustrate slight depressions between adjacent portions of the wire 39 which are eventually filled when the pressure lumens 34, 36 and inflation lumen 38 are added as described below.

Figure 11:
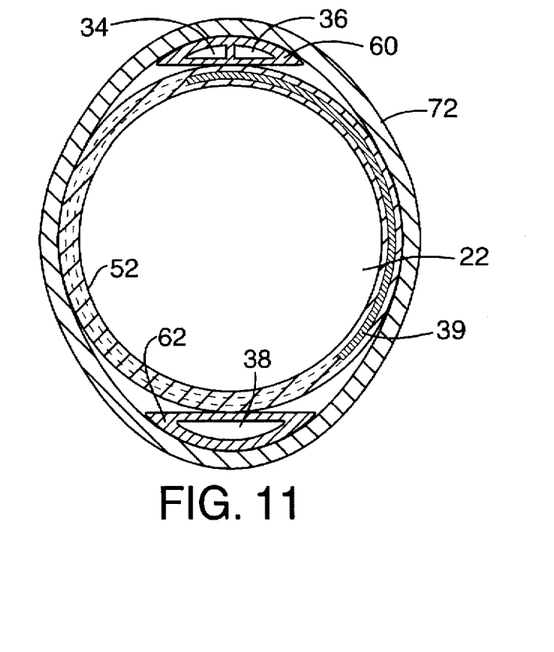
FIG. 11 is a cross-sectional view of the aortic occlusion catheter showing the method of adding pressure lumens and an inflation lumen to the wire reinforced blood flow lumen for the aortic occlusion catheter of FIG. 4.
Figure 12:
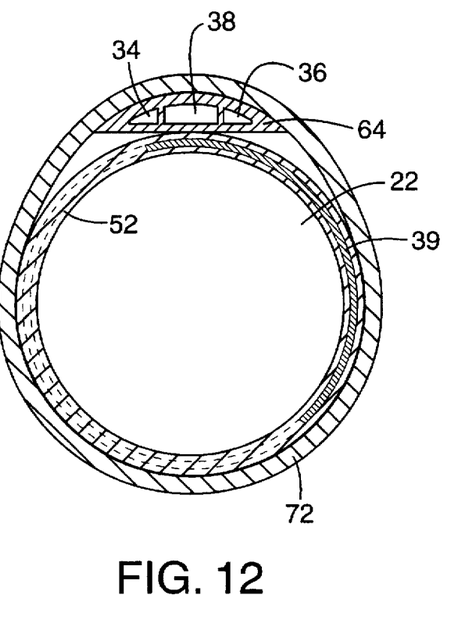
FIG. 12 is a cross-sectional view of the aortic occlusion catheter showing the method of adding pressure lumens and an inflation lumen to the wire reinforced blood flow lumen for the aortic occlusion catheter of FIG. 5.
Figure 13:
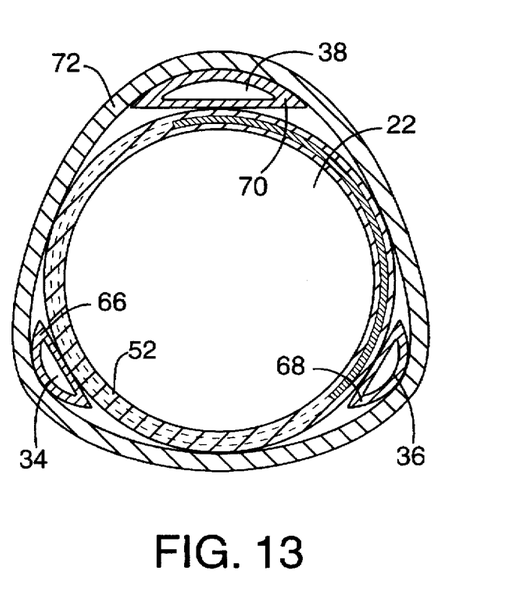
FIG. 13 is a cross-sectional view of the aortic occlusion catheter showing the method of adding pressure lumens and an inflation lumen to the wire reinforced blood flow lumen for the aortic occlusion catheter of FIG. 6.

After formation of the reinforced tubes 52 shown in FIG. 8 and 10, the first and second pressure lumens 34, 36 and the inflation lumen 38 are bonded to the reinforced tube 52. Referring to FIGS. 11–13, the method of constructing the cross-sections shown in FIGS. 4–6, respectively, is shown. FIG. 11 shows the pressure lumens 34, 36 carried together by a D-shaped extrusion 60 which is positioned opposite another D-shaped extrusion 62 for the inflation lumen 38. FIG. 12 shows the pressure lumens 34, 36 and inflation lumen 38 both being carried by a single D-shaped extrusion 64. FIG. 13 shows the pressure lumens 34, 36 and inflation lumen 38 each carried by a separate D-shaped extrusions 66, 68, 70, respectively, with the lumens 34, 36, 38 being spaced 120E apart from one another.

An outer tube 72 is positioned over the pressure lumens 34, 36 and inflation lumen 38. The outer tube 72 is preferably inflated and the reinforced tube 52, pressure lumens 34, 36, and inflation lumen 38 are then positioned inside the outer tube 72. The outer tube 72 is then deflated so that it contracts around the pressure lumens 34, 36, inflation lumen 38 and reinforced tube 52 in the manner shown in FIGS. 11–13. The outer tube 72 is preferably made of the same material as the first and second tubes 54, 56 and has a thickness of between 0.001 and 0.010 inch and more preferably 0.003 inch. A heat shrink tube (not shown) is positioned over the outer tube 72 and the entire structure is heated to form the integrated structures of FIGS. 4–6. The pressure ports 35, 37 in the pressure lumens 34, 36, opening 46 in the inflation lumen 38, and proximal and distal openings 24, 26 in the blood return lumen 22 are then formed. An advantage of adding the pressure lumens 34, 36 and inflation lumen 38 to the outside of the blood return lumen 22 is that the pressure ports 35, 37 and opening 46 in the inflation lumen 38 do not need to be cut through the wire 39.

The aortic occlusion catheter 2 preferably has a soft tip 74 which is made of polyurethane and preferably doped with a radiopaque material so that the position may be visualized using fluoroscopy. The soft tip 74 is bonded to the end of the shaft 40 after forming the reinforced tube 52 so that the tip 74 does not include the wire 39 reinforcing. Radiopaque markers 76 are provided on both sides of the occluding member 12 to further aid in visualizing and positioning the catheter 2 and occluding member 12. The distal openings 26 are also formed through the soft tip 74.

While the above is a preferred description of the invention, various alternatives, modifications and equivalents may be used without departing from the scope of the invention. For example, the occluding member 12 can be an expandable member other than a balloon, the orientation of the aortic occlusion catheter 2 may be reversed with the aortic occlusion catheter 2 passing through another artery, such as the left subclavian artery, with the distal end extending into the brachiocephalic artery, and the aortic occlusion catheter 2 may also include a lumen for delivering cardioplegic fluid to the patient's ascending aorta and venting the aortic root. Thus, the above description should not be taken as limiting the scope of the invention which is defined by the claims.

What is claimed is:

1. A method of occluding a patient's ascending aorta and returning oxygenated blood to the patient, comprising the steps of:

providing an aortic occlusion catheter having a shaft, an occluding member mounted to the shaft, a blood flow lumen, a first opening positioned proximal of the occluding member, and a second opening positioned distal to the occluding member, the first and second openings being fluidly coupled to the blood flow lumen;

positioning the aortic occlusion catheter in at least a portion of a patient's brachiocephalic artery;

expanding the occluding member to an expanded condition so that the patient's ascending aorta is thereby occluded;

coupling the blood flow lumen to a source of oxygenated blood; and infusing oxygenated blood from the source of oxygenated blood into the patient though the blood flow lumen and first and second openings.

2. The method of claim 1, wherein:

the expanding step is carried out so that the patient's brachiocephalic artery is occluded at the aortic arch.

3. The method of claim 1, wherein:

the providing step is carried out with the occluding member being a balloon, the balloon being attached to the shaft at a proximal portion and a distal portion, the balloon also being attached to the shaft along a section extending between the proximal and distal portions.

4. The method of claim 1, wherein:

the positioning step is carried out with the aortic occlusion catheter passing through the patient's right subclavian artery.

5. The method of claim 1, further comprising the step of:

creating an opening in an artery of the patient, the opening being created in an artery selected from the group consisting of subclavian and axillary arteries; and inserting the aortic occlusion catheter through the opening.

6. The method of claim 1, further comprising the step of:

measuring a pressure on a side of the occluding member.

7. The method of claim 6, further comprising the step of:

measuring a pressure on the other side of the occluding member.

8. The method of claim 1, further comprising the steps of:

stopping the patient's heart with a cardioplegic fluid;

withdrawing blood from the patient through a venous cannula;

directing the blood withdrawn from the venous cannula to a bypass system and from the bypass system to the blood flow lumen of the aortic occlusion catheter.

* * * * *